United States Patent [19]
Forsstrom

[11] 3,945,412
[45] Mar. 23, 1976

[54] SAMPLE TRANSPORTATION DEVICE
[75] Inventor: Bo Gosta Forsstrom, Jarfalla, Sweden
[73] Assignee: LKB-Produkter AB, Bromma, Sweden
[22] Filed: Feb. 12, 1975
[21] Appl. No.: 549,278

[30] Foreign Application Priority Data
Feb. 18, 1974 Sweden............................ 7402104

[52] U.S. Cl................. 141/130; 23/253 R; 23/259; 198/19
[51] Int. Cl.² ........................................ B65B 43/50
[58] Field of Search ............... 198/19, 25, 136, 209; 141/130, 284, 129, 131–191, 65; 23/253, 259

[56] References Cited
UNITED STATES PATENTS
1,184,530    5/1916   Jackson et al. .................... 198/136

*Primary Examiner*—Houston S. Bell, Jr.

[57] ABSTRACT

Apparatus for transporting sample containers past a treatment position consists of a rotatable stand in which the containers are supported adjacent to each other in a path running from the center of the stand toward its periphery, with a cam operated device for movably supporting a mouthpiece so as to follow the path of the containers as the stand is rotated.

2 Claims, 4 Drawing Figures

SAMPLE TRANSPORTATION DEVICE

The present invention refers to a sample transportation device for successively bringing a number of sample containers past a treatment position, for instance for adding liquid to the containers or sucking liquid from the containers.

In laboratory work different types of automatic transportation devices are used for passing samples past treatment-or measuring positions. One such transportation device are the so-called fraction collectors, i.e., devices where a number of test tubes successively are brought past an output mouthpiece from for instance a chromatography-or electrophoresis column so as to distribute substances separated in the column into different test tubes for further analysis. This type of sample transportation device is usually also suited for use as so-called samplers, i.e., devices where liquid by means of a mouthpiece successively are sucked from a number of test tubes.

A great number of fraction collector designs are known, using different patterns of movement for the test tubes as well as for the mouthpieces. In one such design the test tubes are arranged in concentric rings in a turnable holder, whereby the mouthpiece is radially displaceable between the rings. An example of such a fraction collector is shown in the U.S. Pat. No. 2,894,542.

The drawback of this type of fraction collector is firstly that the driving means for moving the test tubes and the mouthpiece and the synchronization of these movements are rather complicated, and secondly that such fraction collectors usually require a constant turning angle of the test tube holder between the different positions which means that the distance between the test tubes raises with raising radius of the rings. This latter draw-back also occurs at the type of fraction collectors where the tubes are arranged in a spiral and where the radial movement of the mouthpiece is achieved by means of a groove following the spiral and means connected to the mouthpiece follow the groove, as for instance in British patent 1,153,069.

It is an object of the present invention to provide a sample transportation device suitable for use as a fraction collector in which a sample holder means is turned so as to make the different sample holders successively pass a movable mouthpiece whereby the design is very simple and permits all sample holders to be located close to one another. The characteristics of the invention will appear from the claims attached to the specification.

The invention will now be described in detail reference being made to the enclosed drawing in which.

Figure 1A:
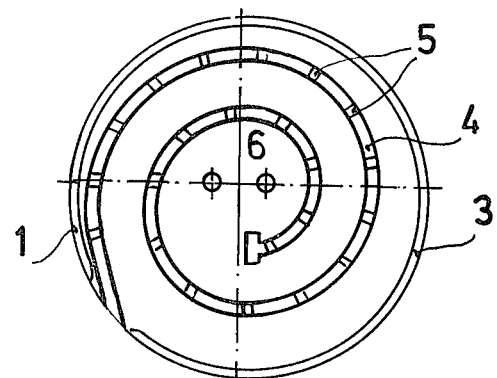
FIG. 1a - 1c shows a sample holder stand used in the invention.
Figure 1B:
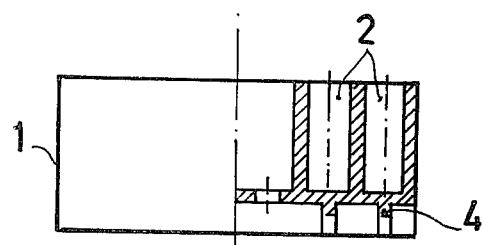
Figure 1C:
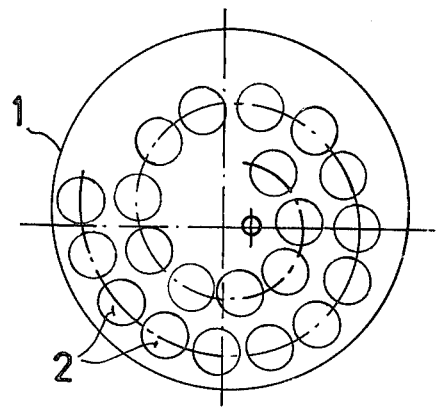

In FIG. 1a - 1c there is shown a sample holder stand according to the invention seen from below, from the side and from above. The stand, denoted 1, consists of a cylindrical body preferably made of plastics and provided with a number of cylindrical bores 2 in which test tubes are to be arranged. The bores 2 are arranged along a spiral shaped path which runs from the periphery of the stand towards the centre. The bottom surface of the stand is provided with a circular outer edge 3, and with a cam 4 which runs along the centres of the bores 2. The cam 4 is provided with some type of markings, for example recesses 5 arranged under the centre of the respective bores 2. At the bottom of the stand there is furthermore arranged two holes 6 for attaching the stand to some suitable driving means as will be explained in connection with FIG. 2.

Figure 2:
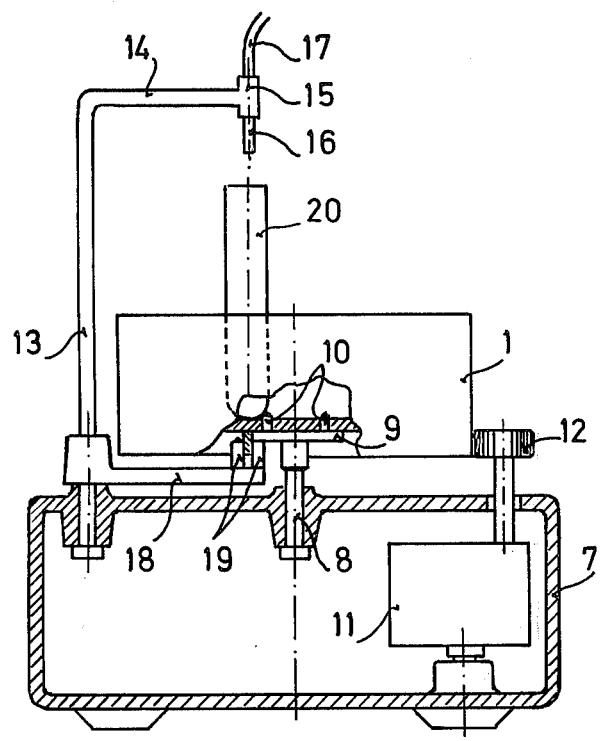
FIG. 2 shows an embodiment according to the invention.

In FIG. 2 which shows an embodiment of the invention reference 7 denotes an instrument body provided with a turnable axis 8, the upper end is provided with a plate 9 having two pins 10. On the plate 9 the stand of FIG. 1 is arranged so that the pins 10 intrude into the holes 6. The body 7 is furthermore provided with a motor 11 which drives a pully 12 which bears on the stand 1 so that this stand can be turned by the motor. The apparatus further comprises an axle 13 journalled in the body and provided with an upper arm 14 and a lower equally long arm 18 which runs between the stand and the body. The arm 14 could for instance be provided with a mouthpiece 16 arranged in a holder 15, liquid being fed to the mouthpiece via a tubing 17. The arm 18 is at its end provided with a fork consisting of two vertical pins 19 which clasp the cam 4 of the stand 1. In the fork are thereby arranged two not shown means for detecting the markings 5. These means could be designed in a manner known per se for providing some type of electrical indication when the fork 19 passes a marking. For instance one pin of the fork could be provided with a light source and the other pin with a photo diode so that light from the light source meets the diode when the fork reaches a marking.

The above described device works as follows. When starting the device a stand 1 filled up with test tubes 20 is placed on the plate 9 with the fork 19 placed at one end of the cam 4. Then the motor 11 is started and the stand starts turning whereby the fork follows the cam 4 and thus the mouthpiece 16 will describe a curve passing over the centres of the different test tubes. When the fork reaches the first marking 5 the detecting device of the fork gives rise to an electrical signal and by means of which the motor is stopped. The electrical circuits necessary for this are known per se and will not be described in detail. The mouthpiece 16 is now above the first test tube and thus liquid could be supplied through the tube. When the first test tube has been filled with a desired amount of liquid the motor is again started for instance by a signal from a timer and the fork 19 guides the mouthpiece 16 so that this is brought to the next test tube whereby the motor is again stopped in the same way as at the first test tube. It should be noted that a number of different principles could be used for triggering the change of test tubes. Thus a detected change of the composition of the liquid could initiate a start of the motor.

According to the invention there is thus provided a very simple and cheap sample transportation device which admits all test tubes to be located close to one another and which furthermore without any modifications of the instrument itself could be used for test tubes of different sizes by using different test tube stands.

We claim:

1. Transportation device for successively moving a number of sample containers past a treatment position, for instance for adding liquid to the containers or sucking liquid from the containers, characterized in that it comprises a rotably journalled sample container stand in which the sample containers are arranged along a path running from the centre of the stand towards its periphery, the stand being provided with a guiding track running along the sample container path, the track being provided with a marking at each sample container, driving means for rotating the stand and two mechanically linked means which are radially displaceable along the stand, one of said means being provided with a mouthpiece and the other being provided with a track follower and also with means for detecting the markings and for generating a signal to stop the driving means at such a detection.

2. Sample transportation device according to claim 1, characterized in that said path is a spiral.

* * * * *